United States Patent
Groiso (10) Patent No.: US 8,372,075 B2
(45) Date of Patent: Feb. 12, 2013

(54) OSTEOSYNTHESIS CLIP AND INSERTION TOOL FOR USE WITH BONE TISSUE FRAGMENTS

(75) Inventor: Jorge A Groiso, Buenos Aires (AR)

(73) Assignee: Medicrea International (FR)

(*) Notice: Subject to any disclaimer, the term of this patent is extended or adjusted under 35 U.S.C. 154(b) by 419 days.

(21) Appl. No.: 12/629,789

(22) Filed: Dec. 2, 2009

(65) Prior Publication Data

US 2010/0082030 A1   Apr. 1, 2010

Related U.S. Application Data

(62) Division of application No. 10/634,410, filed on Aug. 5, 2003, now Pat. No. 7,635,367.

(51) Int. Cl.
*A61B 17/64* (2006.01)
(52) U.S. Cl. .......................................... 606/75
(58) Field of Classification Search ............ 606/72, 606/75, 115, 151, 154–157, 215, 217, 219–221
See application file for complete search history.

(56) References Cited

U.S. PATENT DOCUMENTS

| | | |
|---|---|---|
| 211,404 A | 1/1879 | Pankonin |
| 4,456,006 A | 6/1984 | Wevers et al. |
| 4,887,601 A | 12/1989 | Richards |
| 5,246,443 A * | 9/1993 | Mai .................................. 606/78 |
| 5,366,479 A | 11/1994 | McGarry et al. |
| 5,449,359 A | 9/1995 | Groiso |
| 5,660,188 A | 8/1997 | Groiso |
| 5,827,283 A | 10/1998 | Groiso et al. |
| 5,853,414 A | 12/1998 | Groiso |
| 5,947,999 A | 9/1999 | Groiso |
| 5,993,476 A | 11/1999 | Groiso |
| 6,767,356 B2 | 7/2004 | Kanner et al. |
| 6,773,437 B2 | 8/2004 | Ogilvie et al. |
| 7,635,367 B2 * | 12/2009 | Groiso ............................ 606/75 |
| 2003/0167072 A1 * | 9/2003 | Oberlander .................... 606/232 |
| 2005/0273108 A1 | 12/2005 | Groiso |

* cited by examiner

*Primary Examiner* — Kevin T Truong
*Assistant Examiner* — Michael Araj
(74) *Attorney, Agent, or Firm* — Ostrolenk Faber LLP (57) ABSTRACT

An osteosynthesis clip for the cicatrization of bone tissue fragments. The clip includes at least two engagement legs extending approximately parallel to one another and including respective distal bridging tips and respective proximal insertion tips to be inserted into the bone tissue fragments; and a connecting bridge coupled to the distal bridging tips of the two engagement legs, the connecting bridge including at least two elongated sections extending along side one another, the elongated sections extending along a non-linear trajectory to form a non-linear deformable region, such as a depression or a dome. The engagement legs include helical screw surfaces to facilitate removal of the clip after the bone tissue fragments have fused.

9 Claims, 8 Drawing Sheets

OSTEOSYNTHESIS CLIP AND INSERTION TOOL FOR USE WITH BONE TISSUE FRAGMENTS

CROSS-REFERENCE TO RELATED APPLICATIONS

The present application is a divisional under 37 C.F.R. §1.53(b) of prior application Ser. No. 10/634,410, filed Aug. 5, 2003, by Jorge A. Groiso entitled OSTEOSYNTHESIS CLIP AND INSERTION TOOL FOR USE WITH BONE TISSUE FRAGMENTS.

FIELD OF THE INVENTION

The present invention relates to an osteosynthesis clip, a method for inserting the osteosynthesis clip into bone tissue fragments, and an insertion tool for inserting the osteosynthesis clip into bone tissue fragments.

BACKGROUND INFORMATION

Various elements (e.g., casts and internal elements, such as screws, plates, clips, etc.) and methods are known for permitting the cicatrization of bone parts and/or fragments by holding them together and avoiding their relative movement insofar as possible. For example, U.S. Published Pat. Nos. 5,449,359, 5,660,188, 5,947,999, 5,853,414, and 5,993,476, the entire contents of all of which are expressly incorporated herein by reference, refer to elastic clips and methods for osteosynthesis that prevent bone fragments from moving with respect to one another after insertion of the elastic clips. As characterized, bone fragments to be joined are first drilled in locations for later receiving respective engagement legs of the elastic clip. Once the ends of the legs are inserted into the bone fragments, the elastic clip is grasped by an instrument, and, using a suitable percussion tool, the instrument is struck to push the clip into the bone fragments. Once inserted, the elongated bridge sections of the clip are separated by the tool, which causes the legs to approach one another, thereby carrying the bone fragments into frictional contact under pressure.

It has been found that, if the elongated bridge sections of the clip are over-separated (i.e., separated too much), for example, by a surgeon applying too much separation force on the elongated sections, the contact pressure between the bone tissue fragments in an area near the top surfaces of the bone tissue fragments may exceed the contact pressure between bone tissue fragments in an area near the bottom surfaces of the bone tissue fragments. This may cause the bone tissue fragments to pivot upwardly toward the top of the clip, thereby causing a deviation of the longitudinal axis of the bone fragments and a formation of gap between the fragments.

SUMMARY OF THE INVENTION

It is an object of the present invention to avoid the disadvantages of prior art osteosynthesis clip described above. For this purpose, the present invention provides an osteosynthesis clip for the healing of bone tissue fragments, in which the clip includes at least two engagement legs extending approximately parallel to one another and including respective distal bridging tips and respective proximal insertion tips to be inserted into the bone tissue fragments; and a connecting bridge coupled to the distal bridging tips of the two engagement legs, the connecting bridge including at least two elongated sections extending along side one another, the elongated sections extending along a non-linear trajectory to form a non-linear deformable region, for example, a non-linear depression. In another exemplary embodiment of the present invention, the connecting bridge of the osteosynthesis clip includes a single elongated section extending along a non-linear trajectory to form a non-linear deformable region, for example, a non-linear depression.

By providing the elongated sections of the clip with a non-linear deformable region, such as a depression, a force, such as an upward force, may be applied on the elongated sections of the clip after inserting the clip into the bone fragments. The force causes at least a partial linearization of the non-linear deformable region. This causes the proximal insertion tips to pivot toward one another about the distal bridging tips, thereby causing any gap to close between the bottom surfaces of bone tissue fragments.

It is another object of the present invention to provide an insertion tool to insert an osteosynthesis clip into bone fragments. The tool includes an arrangement to separate the elongated sections of the clip; and an arrangement to apply a force, such as an upward force, on the elongated sections of the clip in an area of the non-linear deformable region, for example, a non-linear depression. In one exemplary embodiment of the present invention, the arrangement to separate the elongated sections includes first and second handles, respective engagement arms coupled to the handles, respective engagement flanges coupled to the respective engagement arms to engage the elongated sections of the clip, pivot arms respectively and pivotally coupled to the handles, and a first biasing arrangement configured to bias the first and second handles into a normally opened position, and the arrangement to apply a force, such as an upward force, on the elongated sections of the clip includes a spacing bolt, a guiding bolt coupled to pivot arms, a pair of pushing plates slidably coupled to guiding bolt, a third handle pivotally coupled to the pushing plates and to the second handle via a pivot pin, and a second biasing arrangement configured to bias the second and third handles into a normally opened position. It should also be appreciated that the insertion tool need not include an arrangement to separate the elongated sections of the clip, if the connecting bridge of the clip includes only a single elongated section extending along a non-linear trajectory to form a non-linear deformable region, for example, a non-linear depression.

DETAILED DESCRIPTION

Figure 1:
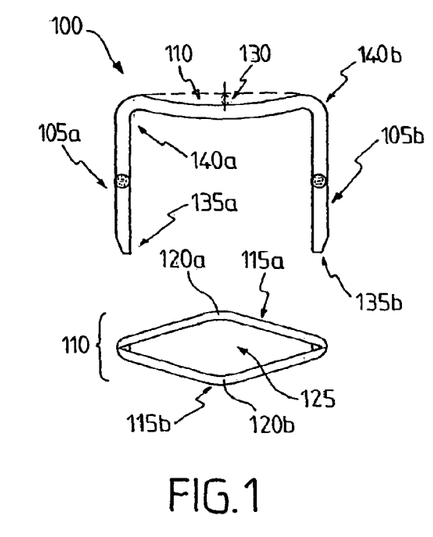
FIG. 1 illustrates a first exemplary osteosynthesis clip according to the present invention.
Figure 2:
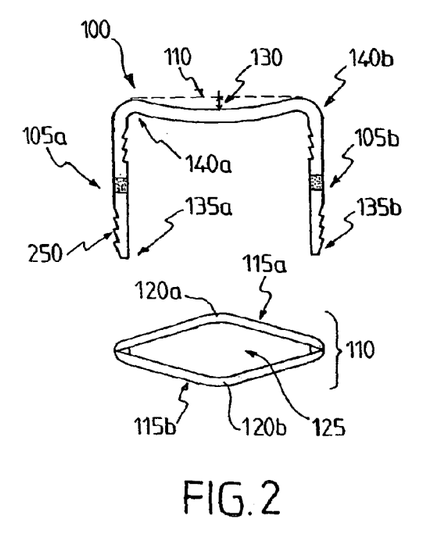
FIG. 2 illustrates a second exemplary osteosynthesis clip according to the present invention having gripping surfaces to frictionally engage the bone tissue.
Figure 4A:
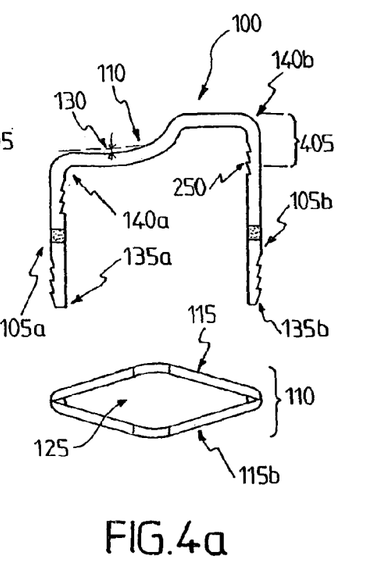
FIGS. 4a and 4b illustrate a third exemplary osteosynthesis clip according to the present invention having a stepped-up section to set bone fragments having varying diameters.
Figure 4B:
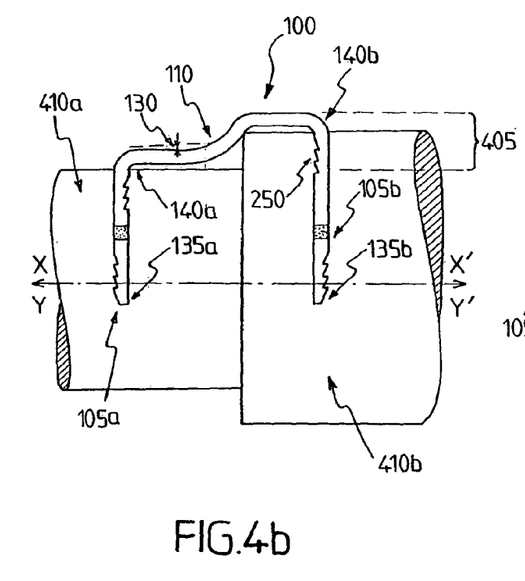

Referring now to FIG. 1, there are seen side and top views, respectively, of a first exemplary elastic osteosynthesis clip 100 according to the present invention. Osteosynthesis clip 100 includes at least two engagement legs 105a, 105b and a connecting bridge 110 to couple engagement legs 105a, 105b to one another, thereby forming a unitary clip 100. Engagement legs 105a, 105b extend approximately parallel to one another and include respective proximal insertion tips 135a, 135b for insertion into the bone tissue and respective distal bridging tips 140a, 140b for coupling to bridge 110. Engagement legs 105a, 105b may have any cross section (e.g., round, square) suitable for insertion into bone, and may be provided with gripping surfaces 250 (e.g., gripping teeth) to frictionally engage the bone tissue (not shown), as shown in FIGS. 2, 4a, and 4b.

The clip 100 may be made of any material suitable for insertion into living tissue (e.g., bone tissue). For example, clip 100 may be made of a biocompatible material (e.g., stainless steel alloy or a titanium alloy metal such as TA6V of medical grade) having suitable elasticity and mechanical strength.

Bridge 110 includes two elongated sections 115a, 115b extending along side one another. The sections 115a, 115b include respective bulges 120a, 120b, which together form a space 125 of separation between elongated sections 115a, 115b. As seen in the side view of clip 100 in FIG. 1, elongated sections 115a, 115b extend side by side one another along a non-linear trajectory, thereby forming a non-linear deformable region 130, such as a depression 130. Deformable region 130 is provided to facilitate clamping of bone tissue fragments (not shown), as more fully described below. Elongated sections 115a, 115b of bridge 110 may also be provided with a stepped-up section 405, as shown in FIG. 4a. In this manner, clip 100 may be used to set bone fragments 410a, 410b having varying diameters, so that the axes of bone fragments 410a, 410b align with one another, as shown in FIG. 4b.

Figure 10:
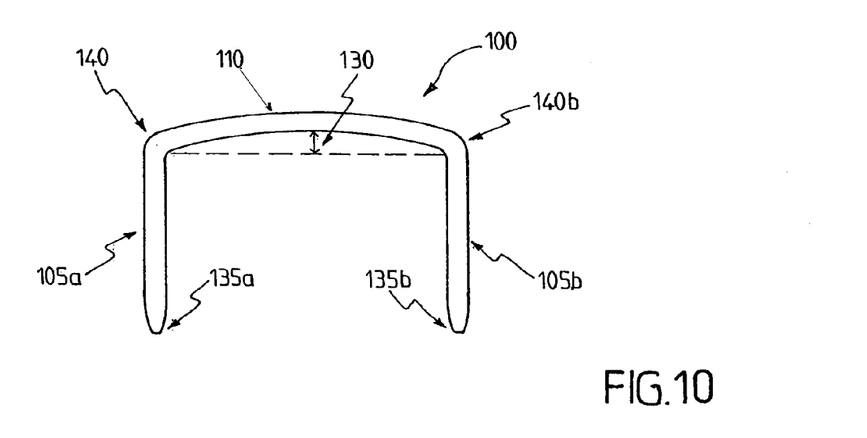
FIG. 10 illustrates a variant of the osteosynthesis clip of FIG. 1 having a dome-shaped non-linear deformable region.

Referring now to FIG. 10, there is seen a variant of exemplary elastic osteosynthesis clip 100 of FIG. 1. In this exemplary variant according to the present invention, non-linear deformable region 130 is provided in the form of dome 130, instead of a depression.

Figure 8A:
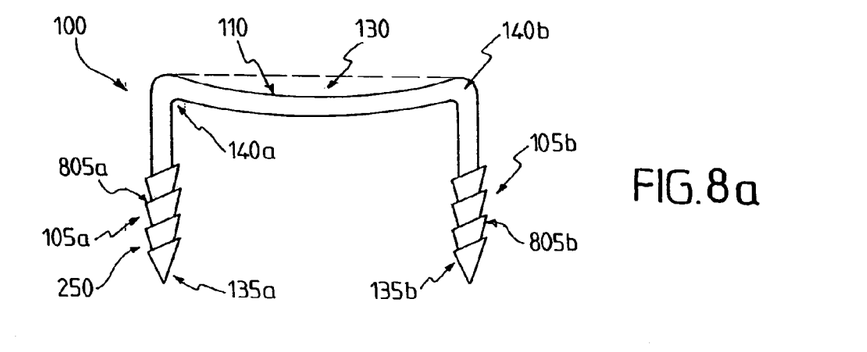
FIG. 8a through 8c illustrate an operational sequence for removing a variant of the exemplary osteosynthesis clip of FIG. 1 after bone tissue has fused.
Figure 8B:
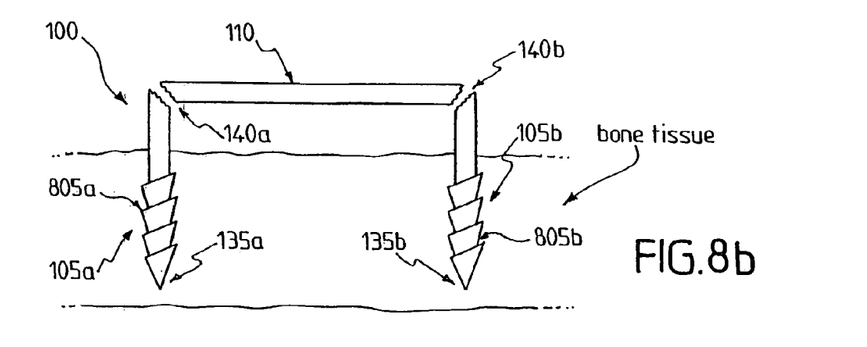
Figure 8C:
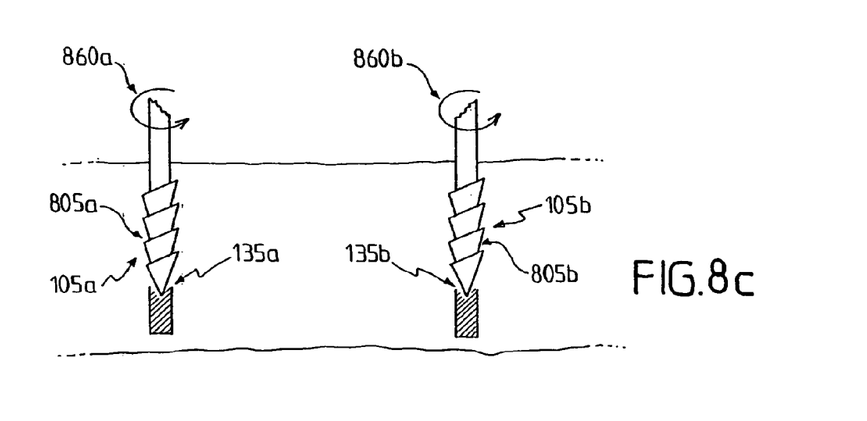
Figure 9:
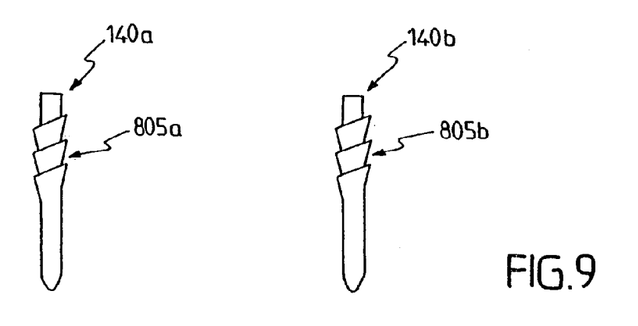
FIG. 9 illustrates a variant of the osteosynthesis clip shown in FIGS. 8 through 8c.

Referring now to FIG. 8a, there is seen a variant of the exemplary elastic osteosynthesis clip 100 according to the present invention. In this exemplary embodiment, clip 100 includes gripping surfaces 250 in the form of helical screw surfaces 805a, 805b provided near proximal insertion tips 135a, 135b to frictionally engage the bone tissue (not shown). In addition, engagement legs 105a, 105b of clip 100 may be provided with any desired cross-section, such as a round cross-section, a square cross-section, an elliptical cross-section, etc. In this exemplary embodiment, engagement legs 105a, 105b are provided with helical screw surfaces 805a, 805b, which advantageously facilitate the removal of clip 800 after the bone tissue (not shown) has been fused. For this purpose, clip 800 may be cut in the locations of distal bridging tips 140a, 140b to remove bridge 110, as shown in FIG. 8b. Once bridge 110 is removed, engagement legs 105a, 105b may be removed from the bone tissue, for example, by unscrewing engagement legs 105a, 105b in a counterclockwise direction 860a, 860b, as shown in FIG. 8c. FIG. 9 illustrates another variant of the osteosynthesis clip 100 shown in FIGS. 8a through 8c. In this exemplary embodiment, helical screw surfaces 805a, 805b are provided on an area of engagement legs 105a, 105b disposed toward distal bridging tips 140a, 140b. It should also be appreciated that helical screw surfaces 805a, 805b may be provided near proximal insertion tips 135a, 135b and near distal bridging tips 140a, 140b of engagement legs 105a, 105b.

Figures 3A, 3B:
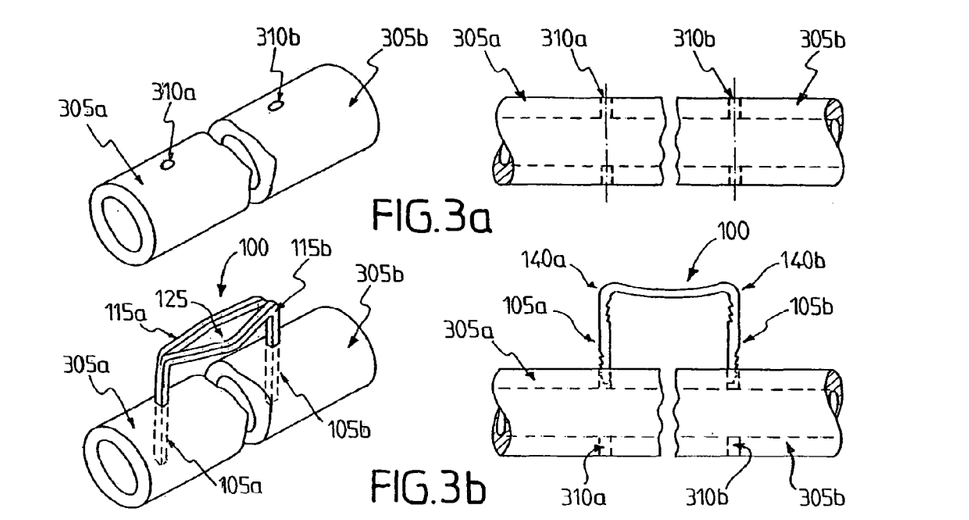
FIGS. 3a through 3d show an operational sequence for inserting an osteosynthesis clip to couple bone tissue fragments.
Figure 3C:
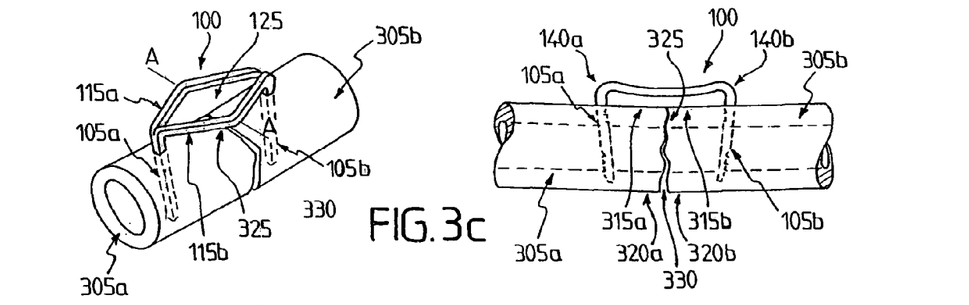

Referring now to FIG. 3a through 3d, there is seen an operational sequence for inserting osteosynthesis clip 100 with a depression 130 to couple bone tissue fragments 305a, 305b. As shown in FIG. 3a, bone fragments 305a, 305b are pre-drilled with respective clip reception holes 310a, 310b for respectively receiving engagement legs 105a, 105b of osteosynthesis clip 100. After drilling holes 310a, 310b, osteosynthesis clip 100 is inserted into bone tissue fragments 305a, 305b, as shown in FIG. 3b. For this purpose, clip 100 may be coupled to an instrument (not shown), and a percussion force may be applied to the instrument (not shown) to drive clip 100 into bone tissue fragments 305a, 305b. Once clip 100 is fully inserted into bone tissue fragments 305a, 305b, the elongated sections 115a, 115b are separated, for example, by the instrument and/or a separate tool (not shown), as shown in FIG. 3c. This causes space 125 of clip 100 to widen along line A, thereby causing engagement legs 105a, 105b to approach one another to cause bone tissue fragments 305a, 305b to come in contact with one another under pressure. If bone tissue fragments 305a, 305b come in contact with one another under too high a pressure, elongated sections 115a, 115b may be brought closer together. This causes space 125 of clip 100 to narrow along line A, thereby causing engagement legs 105a, 105b to separate from one another.

If elongated sections 115a, 115b are over-separated (i.e., separated too much), for example, by a surgeon applying too much separation force on elongated sections 115a, 115b, the contact pressure between bone tissue fragments 305a, 305b in an area near the top surfaces 315a, 315b of bone tissue fragments 305a, 305b may exceed the contact pressure between bone tissue fragments 305a, 305b in an area near the bottom surfaces 320a, 320b of bone tissue fragments 305a, 305b. This may cause bone tissue fragments 305a, 305b to pivot upwardly about contact pivot surface 325, thereby causing engagement legs 105a, 105b of clip 100 to pivot away from one another about distal bridging tips 140a, 140b. In this manner, the longitudinal axes of the bone tissue fragments 305a, 305b become unaligned and a gap 330 forms between the fragments 305a, 305b. In this case, merely bringing elongated sections 115a, 115b closer together to separate bone tissue fragments 305a, 305b may not help alleviate the problem.

Figure 3D:
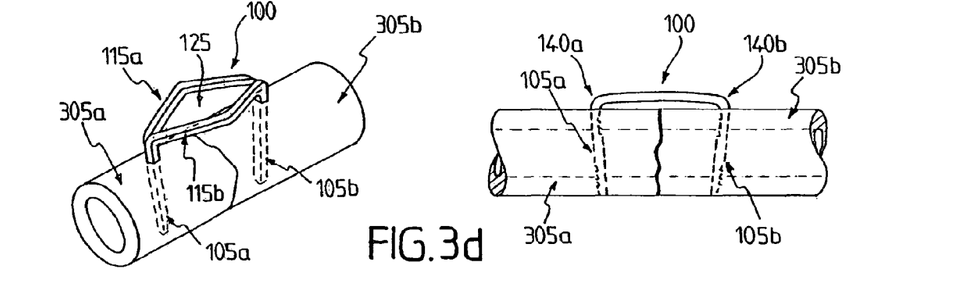

To close gap 330 and to ensure proper setting of bone tissue fragments 305a, 305b, a force, such as an upward force, is applied to elongated sections 115a, 115b of clip 100 in an area of non-linear deformable region 130, as shown in FIG. 3d. While applying the force to elongated sections 115a, 115b, withdrawal of clip 100 may be prevented by simultaneously applying an opposing force, such as a downward force, on distal bridging tips 140a, 140b. The force applied to elongated sections 115a, 115b of clip 100 causes at least a partial linearization of non-linear deformable region 130. This causes proximal insertion tips 135a, 135b to pivot toward one another about distal bridging tips 140a, 140b, thereby causing gap 330 to close between the bottom surfaces 320a, 320b of bone tissue fragments 305a, 305b, as shown in FIG. 3d.

If the osteosynthesis clip 100 is provided with a dome 130, as shown in FIG. 10, the operational sequence of FIGS. 3a through 3d may be performed to couple bone tissue fragments 305a, 305b with only minor modification. Specifically, after inserting clip 100 into bone tissue fragments 305a, 305b, a downward force is applied to elongated sections 115a, 115b in an area of non-linear deformable dome 130, before elongated sections 115a, 115b are separated. The downward force applied to elongated sections 115a, 115b of clip 100 causes elongated sections 115a, 115b to move away from one another. After applying the downward force, elongated sections 115a, 115b of clip 100 may be separated to cause engagement legs 105a, 105b to approach one another, thereby causing bone tissue fragments 305a, 305b to come in contact with one another under pressure. This operational sequence may be required when operating on bone having a pronounced tendency to axial flexion angulation (e.g., metacarpals). Clip 100 of FIG. 10 may be applied, for example, to the dorsum of the hand. The axes of the bone tissue fragments 305a, 305b may be corrected by flattening non-linear deformable dome 130 of bridge 110, and bone tissue fragments 305a, 305b may be brought together by separating elongated sections 115a, 115b, as described above.

Referring now to FIGS. 5a through 5i, there is seen a first exemplary fixation tool 500 configured to insert clip 100 into bone tissue fragments 305a, 305b. Fixation tool 500 includes handles 505a, 505b, a set of engagement arms 515a, 515b respectively coupled to handles 505a, 505b, pivot arms 510a, 510b respectively and pivotally coupled to handles 505a, 505b, a first biasing arrangement 520 (e.g., a pair of biased spring clips, a spring, etc.) configured to bias handles 505a, 505b in a normally opened position, a spacing bolt 525, a guiding bolt 530 coupled to pivot arms 510a, 510b, a pair of pushing plates 535a, 535b slidably coupled to guiding bolt 530, a handle 505c pivotally coupled to pushing plates 535a, 535b and to handle 505b via pivot pin 550, and a second biasing arrangement 540 (e.g., a pair of biased spring clips, a spring, etc.) configured to bias handles 505b, 505c in a normally opened position.

Fixation tool 500 may be used to perform the operational sequence shown in FIG. 3a through 3d for inserting osteosynthesis clip 200 to couple bone tissue fragments 305a, 305b. After drilling holes 310a, 310b, osteosynthesis clip 100 is inserted into bone tissue fragments 305a, 305b, for example, using fixation tool 500. For this purpose, engagement arms 515a, 515b of fixation tool 500 are provided with respective engagement flanges 545a, 545b for fixedly engaging elongated sections 115a, 115b of clip 100. Once clip 100 is coupled to fixation tool 500, osteosynthesis clip 100 is inserted into bone tissue fragments 305a, 305b, as shown in FIG. 3b. For this purpose, a percussion force, for example, may be applied to handles 505a and/or 505b to drive clip 100 into bone tissue fragments 305a, 305b. Alternatively, it should be appreciated that clip 100 may be inserted into bone tissue fragments 305a, 305b using a separate tool and/or percussion instrument, such as a surgical hammer.

Figures 5A, 5B, 5C:
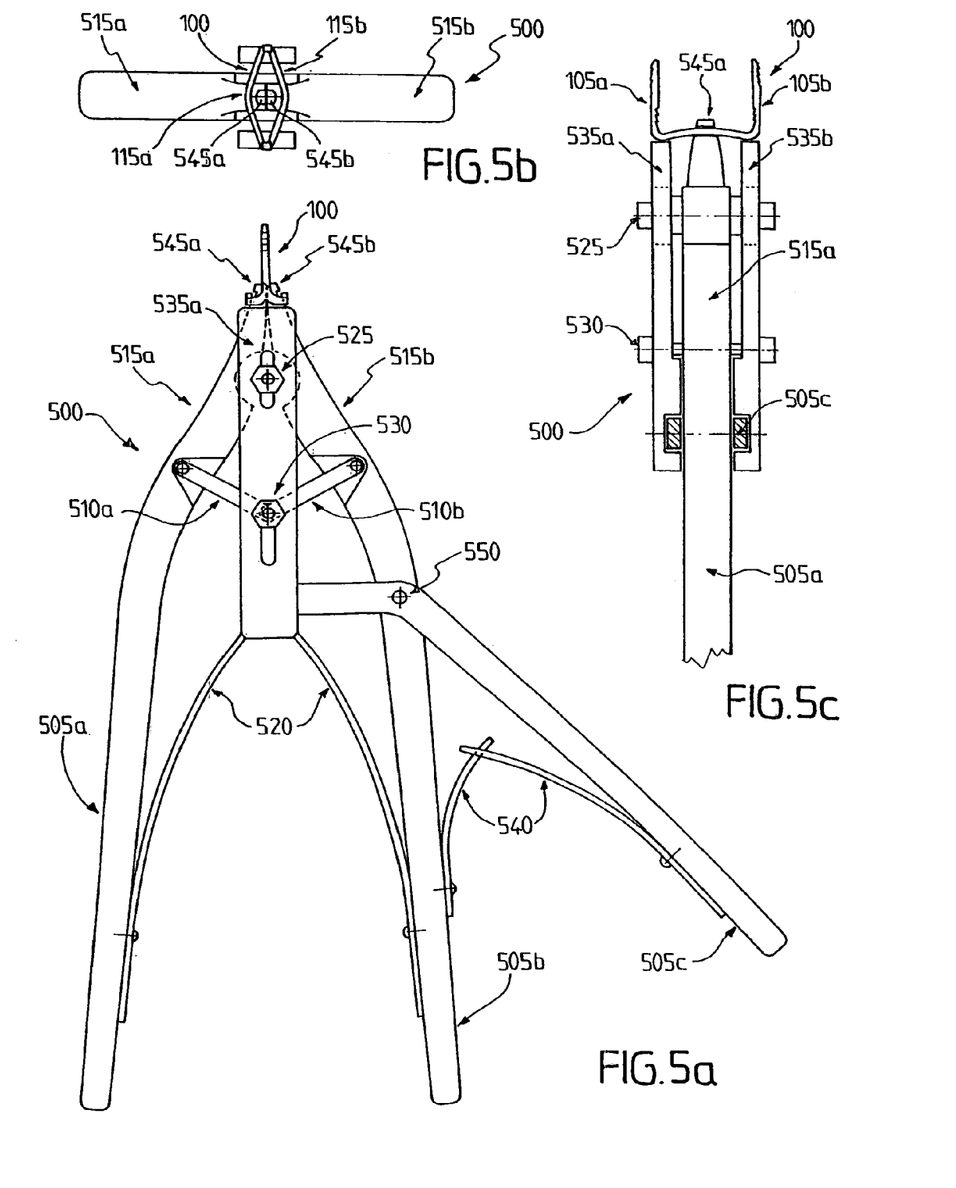
FIGS. 5a through 5i illustrate a first exemplary fixation tool according to the present invention.
Figures 5D, 5E, 5F:
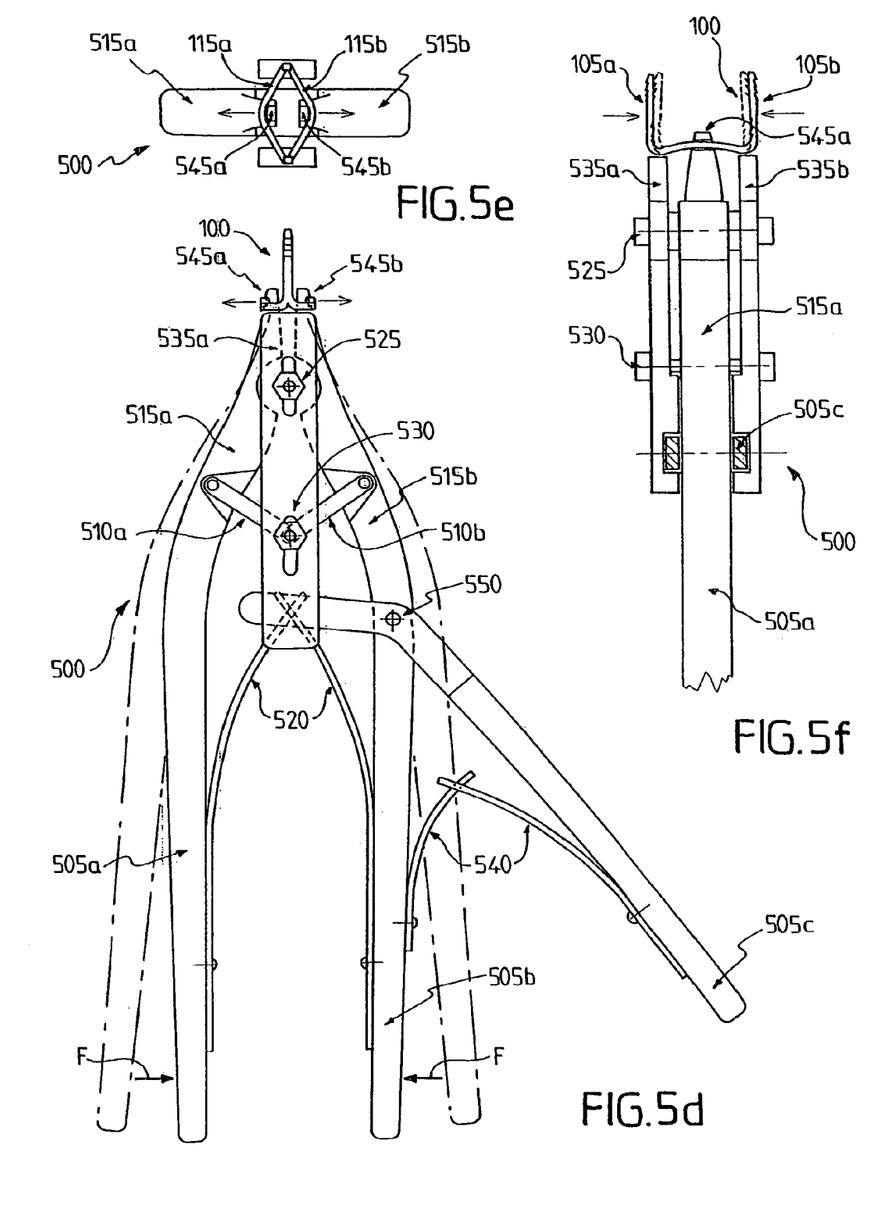

Once clip 100 is fully inserted into bone tissue fragments 305a, 305b, the elongated sections 115a, 115b of clip 100 are separated to cause bone tissue fragments 305a, 305b to contact one another under pressure. For this purpose, a user, for example, a surgeon, applies a first squeezing force to handles 505a, 505b against the biasing force of first biasing arrangement 520, as shown in FIGS. 5d through 5f. This causes handles 505a, 505b to respectively pivot about pivot arms 510a, 510b, thereby causing engagement flanges 545a, 545b of engagement arms 515a, 515b to separate from one another, as shown in FIGS. 5d through 5f. This, in turn, causes space 125 of clip 100 to widen, thereby causing engagement legs 105a, 105b of clip 100 to approach one another to cause bone tissue fragments 305a, 305b to come in contact with one another under pressure.

Figures 5G, 5H, 5I:
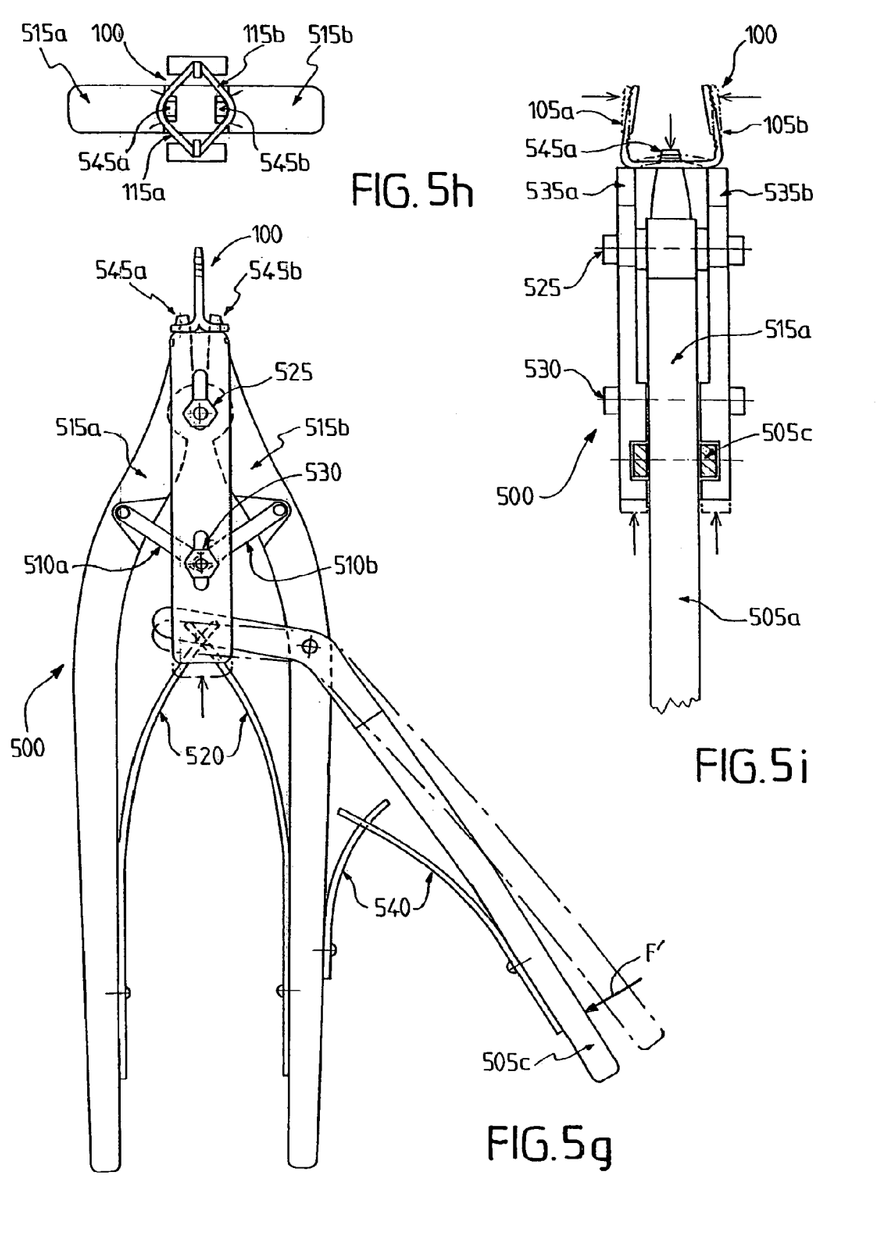

Without releasing the first squeezing force on handles 505a, 505b, the user (e.g., the surgeon) applies a second squeezing force to handles 505b, 505c against the biasing force of second biasing arrangement 540, as shown in FIGS. 5g through 5i. This causes handle 505c to pivot about pivot pin 550, thereby causing pushing plates 535a, 535b to respectively engage distal bridging tips 140a, 140b of clip 100 by sliding distally toward engagement flanges 545a, 545b.

As the user (e.g., the surgeon) continues to apply the second squeezing force to handles 505b, 505c, pushing plates 535a, 535b apply a downward force to distal bridging tips 140a, 140b of clip 100, while engagement flanges 545a, 545b apply an upward force to elongated sections 115a, 115b of clip 100 in an area of non-linear deformable region 130, as shown in FIG. 3d. As described above, the force (e.g., an upward force) applied to elongated sections 115a, 115b of clip 100 causes at least a partial linearization of non-linear deformable region 130 (e.g., non-linear depression 130). This causes proximal insertion tips 135a, 135b to pivot toward one another about distal bridging tips 140a, 140b, thereby causing gap 330 to close between the bottom surfaces 320a, 320b of bone tissue fragments 305a, 305b, as shown in FIG. 3d.

Figure 6:
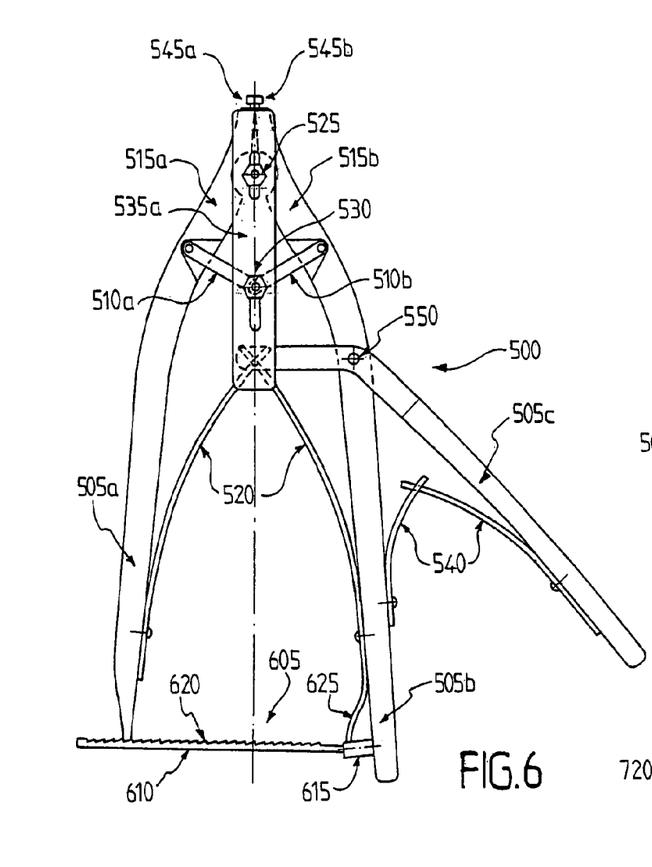
FIG. 6 illustrates a second exemplary fixation tool according to the present invention.

As described above, the second squeezing force is applied to handles 505b, 505c without releasing the first squeezing force on handles 505a, 505b. For this purpose, handle 505b may be provided with a ratchet arrangement 605 configured to prevent handles 505a, 505b from separating from one another after the first squeezing force is applied, as shown in FIG. 6. Ratchet arrangement 605 includes a connecting end 615 coupled to handle 505b, a ratchet clip 610 provided with ratchet teeth 620, and a third biasing arrangement 625 configured to bias at least a portion of ratchet clip 610 toward engagement arms 515a, 515b (e.g., a third biasing arrangement 625 configured to bias end 606 of ratchet clip 610 toward the bottom end of handle 505a). In this manner, as the user (e.g., the surgeon) applies the first squeezing force to handles 505a, 505b, ratchet teeth 620 of ratchet clip 610 engage with the bottom of handle 505a, thereby preventing handles 505a, 505b from separating from one another as the second force is applied to handles 505b, 505c.

After the second squeezing force is applied to handles 505b, 505c and clip 100 is properly inserted into bone tissue fragments 305a, 305b, handle 505a is released from teeth 620 of ratchet clip 510. For this purpose, the user (e.g., the surgeon) applies a force to end 606 of ratchet clip 610 in a direction against the biasing force of third biasing arrangement 625. In this manner, teeth 620 of ratchet clip 610 disengage the bottom end of handle 505a, thereby permitting handles 505a, 505b to separate from one another via the biasing force produced by first biasing arrangement 520.

It should be appreciated that the connecting end of the ratchet arrangement may be alternatively coupled to handle 505a instead of handle 505b. In this manner, the third biasing arrangement 625 biases end 606 of ratchet clip 610 toward the bottom end of handle 505b.

Figure 7:
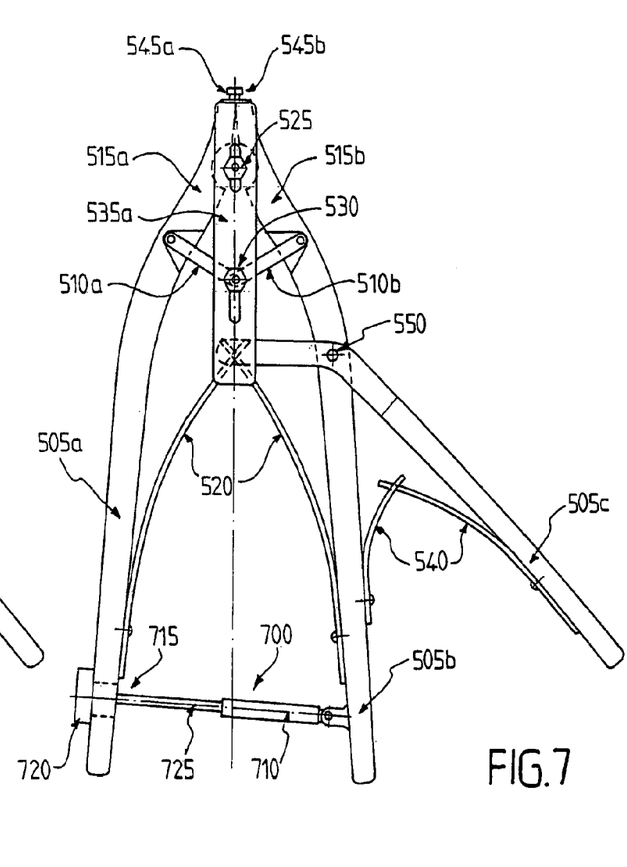
FIG. 7 illustrates a third exemplary fixation tool according to the present invention.

In another exemplary embodiment according to the present invention, fixation tool 500 is provided with a bolt retention arrangement 700 in lieu of ratchet arrangement 605 for preventing handles 505a, 505b from separating from one another after the first squeezing force is applied, as shown in FIG. 7. Bolt retention arrangement 700 includes a bolt receptacle 710 pivotally coupled to handle 505b and a bolt 715 rotationally coupled to handle 505a. Bolt 715 includes a knob portion 720 and a threaded sleeve 725 configured to engage with a threaded inner surface (not shown) of bolt receptacle 710. It should be appreciated that the bolt receptacle 710 may be pivotally coupled to handle 505a instead of handle 505b and bolt 715 may be rotationally coupled to handle 505a instead of handle 505b.

As the user (e.g., the surgeon) applies the first squeezing force to handles 505a, 505b, the user turns knob portion 720 (e.g., in a clockwise direction) to cause threaded sleeve 725 to engage with the threaded inner surface (not shown) of bolt receptacle 710. This causes threaded sleeve 725 to displace within bolt receptacle 710 toward handle 505b. In this manner, bolt retention arrangement 700 prevents handles 505a, 505b from separating from one another as the second force is applied to handles 505b, 505c. After the second squeezing force is applied to handles 505b, 505c and clip 100 is properly inserted into bone tissue fragments 305a, 305b, handle 505a may be released from handle 505b by simply turning knob portion 720 (e.g., in a counter-clockwise direction) to cause threaded sleeve 725 to displace within bolt receptacle 710 away from handle 505b.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A removable osteosynthesis clip for the cicatrization of bone tissue fragments, the clip comprising:
    at least two straight engagement legs extending parallel to one another in a first direction and including respective bridging tips and respective insertion tips adapted to be inserted into the bone tissue fragments; and
    a connecting bridge coupled to the bridging tips of the two engagement legs, the connecting bridge including at least two elongated sections extending along side one another generally in a second direction substantially perpendicular to the first direction, the elongated sections having a non-linear outline having a curved shape forming a non-linear deformable region when viewed in a third direction perpendicular to said first and second directions, such that the non-linear deformable region has a curved shape extending upwardly or downwardly in the first direction, the curved shape extending over at least half the length of the elongated section,
    wherein the elongated sections of the clip receive a force in the first direction in an area of the non-linear deformable region to substantially straighten the non-linear deformable region and cause the insertion tips to pivot,
    the engagement legs being provided with respective helical screw surfaces to facilitate removal of the clip after the bone tissue fragments have fused.

2. The osteosynthesis clip of claim 1, wherein the non-linear deformable region includes one of a depression and a dome.

3. The osteosynthesis clip of claim 1, wherein the two elongated sections include respective bulges that together form a space of separation between elongated sections.

4. The osteosynthesis clip of claim 1, wherein the engagement legs and the connecting bridge are constructed from a biocompatible material.

5. The osteosynthesis clip of claim 1, wherein the elongated sections include respective stepped-up sections to permit the setting of bone fragments having varying diameters.

6. The osteosynthesis clip of claim 1, wherein the helical screw surfaces are provided on only a portion of the lengths of the engagement legs, thereby to facilitate removal of the clip after the bone tissue fragments have fused.

7. A removable osteosynthesis clip for the cicatrization of bone tissue fragments, the clip comprising
    at least two straight engagement legs extending parallel to one another in a first direction and including respective bridging tips and respective insertion tips adapted to be inserted into the bone tissue fragments; and
    a connecting bridge coupled to the bridging tips of the two engagement legs, the connecting bridge including at least two elongated sections extending along side one another generally in a second direction substantially perpendicular to the first direction, the elongated sections having a non-linear outline having a curved shape forming a non-linear deformable region when viewed in a third direction perpendicular to said first and second directions,
    wherein the elongated sections of the clip receive a force in the first direction in an area of the non-linear deformable region to substantially straighten the non-linear deformable region and cause the insertion tips to pivot,
    the engagement legs being provided with respective helical screw surfaces to facilitate removal of the clip after the bone tissue fragments have fused,
    wherein the helical screw surfaces are provided on only a portion of the lengths of the engagement legs, thereby to facilitate removal of the clip after the bone tissue fragments have fused,
    wherein the elongated sections are severed to allow the engagement legs to be unscrewed from the bone tissue.

8. The osteosynthesis clip of claim 7, wherein the helical screw surfaces are provided along only a portion of the legs adjacent the connecting bridge.

9. The osteosynthesis clip of claim 7, wherein the helical screw surfaces are provided along only a portion of the legs adjacent the insertion tips.

* * * * *